(12) United States Patent
Ayre et al.

(10) Patent No.: US 11,439,813 B2
(45) Date of Patent: Sep. 13, 2022

(54) PERCUTANEOUS LEAD

(71) Applicant: Northern Development AS, Oslo (NO)

(72) Inventors: Peter Ayre, New South Wales (AU); John Begg, New South Wales (AU)

(73) Assignee: Northern Development AS, Oslo (NO)

( * ) Notice: Subject to any disclaimer, the term of this patent is extended or adjusted under 35 U.S.C. 154(b) by 155 days.

(21) Appl. No.: 16/564,707

(22) Filed: Sep. 9, 2019

(65) Prior Publication Data

US 2020/0078588 A1   Mar. 12, 2020

(30) Foreign Application Priority Data

Sep. 10, 2018  (AU) ................ 2018903393

(51) Int. Cl.
*A61N 1/05* (2006.01)
*A61M 39/00* (2006.01)

(52) U.S. Cl.
CPC .......... *A61N 1/0595* (2013.01); *A61M 39/00* (2013.01); *A61N 1/0563* (2013.01)

(58) Field of Classification Search
CPC ........ A61N 1/05; A61N 1/0502; A61N 1/056; A61N 1/0563; A61N 1/0595; A61N 1/365; A61N 1/3702; A61N 1/3706; A61N 1/3752; A61N 1/3925; A61N 1/39622; A61M 39/00; A61M 39/0247; A61M 60/148; A61M 60/205; A61M 60/857; A61M 2039/0267; A61M 60/178; H01B 7/048; A61B 5/0004; A61B 5/0006; A61B 5/0031; A61B 5/11; A61B 5/1107; A61B 5/24; A61B 5/283; A61B 5/686; A61B 2562/0219
USPC ........................................................... 607/119
See application file for complete search history.

(56) References Cited

U.S. PATENT DOCUMENTS

| | | |
|---|---|---|
| 4,143,661 A | 3/1979 | Laforge et al. |
| 5,282,845 A | 2/1994 | Bush et al. |
| 5,908,447 A | 6/1999 | Schroeppel et al. |
| 7,745,732 B2 | 6/2010 | Michael et al. |
| 7,803,021 B1 | 9/2010 | Brase |
| 7,983,767 B2 | 7/2011 | Dadd et al. |
| 8,433,424 B2 | 4/2013 | Olson |
| 8,483,823 B2 | 7/2013 | Libbus et al. |
| 8,939,883 B2 | 1/2015 | Callaway et al. |
| 9,272,155 B2 | 3/2016 | Ostroff |

(Continued)

FOREIGN PATENT DOCUMENTS

| | | |
|---|---|---|
| CA | 2027744 C | 5/1999 |
| CN | 102573986 B | 1/2016 |

(Continued)

*Primary Examiner* — Carl H Layno
*Assistant Examiner* — Jane C Kalinock
(74) *Attorney, Agent, or Firm* — Elmore Patent Law Group, P.C.; Joseph C. Zucchero; Carolyn S. Elmore

(57) ABSTRACT

A percutaneous lead assembly for an active implantable device, the lead assembly comprising a sheath with a plurality of wires extending from a proximal end to a distal end. The wires being adapted to power the active implantable device; the distal end having at least one electrode fixed thereon. The electrodes being in communication with sensor electronics and wherein at least one electrode is on the outer layer of the lead assembly in which the electrode is used to detect at least one of acceleration and electrical signals of an organ.

16 Claims, 4 Drawing Sheets

(56) References Cited

U.S. PATENT DOCUMENTS

| | | | |
|---|---|---|---|
| 9,731,111 B2 | 8/2017 | Derohan et al. | |
| 9,827,426 B2 | 11/2017 | Reddy | |
| 10,035,017 B2 | 7/2018 | Thakkar et al. | |
| 10,080,828 B2* | 9/2018 | Wiesener | A61M 60/122 |
| 2011/0118537 A1* | 5/2011 | Wampler | A61M 60/122 |
| | | | 600/17 |
| 2012/0149229 A1* | 6/2012 | Kearsley | A61M 60/857 |
| | | | 439/339 |
| 2017/0304019 A1* | 10/2017 | Sanghera | A61N 1/0504 |
| 2018/0311427 A1* | 11/2018 | Duhamel | A61M 60/871 |
| 2019/0336767 A1* | 11/2019 | Klepfer | A61M 60/148 |
| 2020/0061267 A1* | 2/2020 | Uennigmann | A61M 60/871 |

FOREIGN PATENT DOCUMENTS

| | | |
|---|---|---|
| CN | 104884122 B | 12/2016 |
| EP | 0293499 A1 | 12/1988 |
| EP | 0984664 A1 | 3/2000 |
| EP | 1056507 B1 | 11/2005 |
| EP | 1255584 B1 | 5/2010 |
| EP | 2445577 B1 | 8/2015 |
| ES | 2239083 T3 | 9/2005 |
| JP | 4616252 B2 | 10/2010 |
| JP | 4776132 B2 | 7/2011 |
| JP | 6454728 B2 | 12/2018 |

* cited by examiner

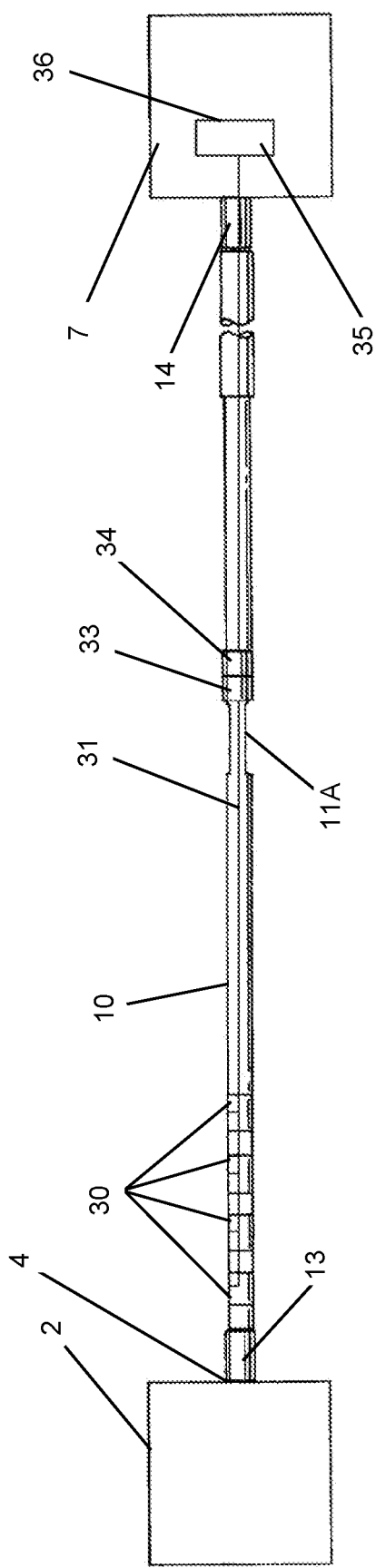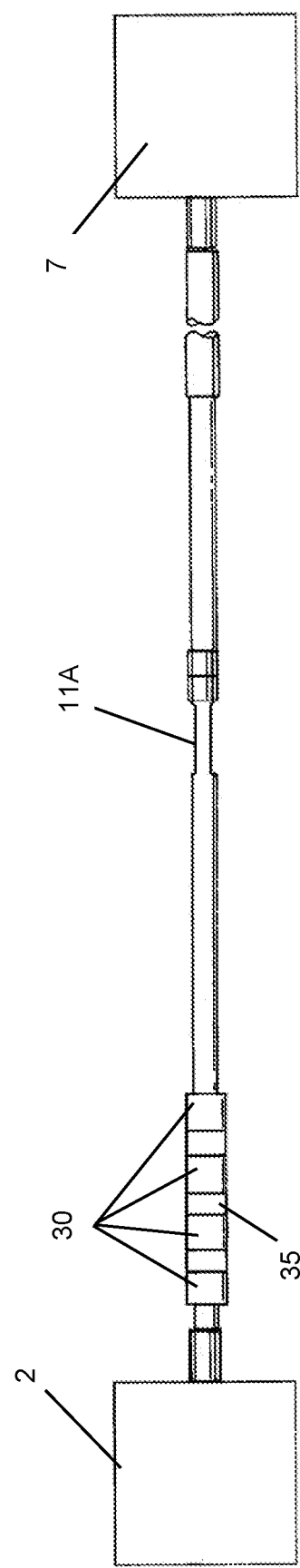
FIG. 4
FIG. 5

PERCUTANEOUS LEAD

RELATED APPLICATION

This application claims priority under 35 U.S.C. § 119 to Australian Application No. 2018903393, filed Sep. 10, 2018. The entire teachings of the above application are incorporated herein by reference.

TECHNICAL FIELD

The present disclosure relates to a lead for insertion into a patient. More particularly, the present disclosure relates to an improved percutaneous lead with at least one sensor.

BACKGROUND

As medical technology improves and the number of older persons increases, there will generally be a greater need for implantable medical devices and components thereof. Some of these implantable medical assist devices passively assist patient's body functions. Examples of passive medical devices include: artificial cannulation to replace or assist failing arteries or veins; and various artificial implants such as artificial blood implants. Other implantable medical devices are called active implantable medical devices. These active implantable medical devices generally require a power source or supply to function or aid the patient's normal bodily functions. These active implantable medical devices may include pacemakers, implantable pumps, neuro-stimulators, and cochlear implants.

There has been a long felt need to be able to safely and reliably implant active medical assist devices and to avoid long term patient problems associated with the use of such devices. One of the common problems encountered with the use of these devices is that a substantial proportion of these generally require a means of communicating electrical information, data, and/or power with the external environment outside the body of a patient, when implanted.

The traditional solution for this problem is to connect the implanted active medical device to a percutaneous lead. This lead will generally extend from the implanted device within the body of the patient, through the skin layer of a patient then to a controller, computer or power circuit (external to the body of the patient). This traditional configuration may lead to increased risk of bacterial infection and reduced quality of life for the patient. Additionally there is a risk that said lead may be accidentally severed by the patient and this raises safety and reliability concerns relating to the traditional use of percutaneous leads.

The human heart is a complex and critical pump. Due to various pathologies, the heart can become dysfunctional, acutely or chronically. When damage to the heart becomes sufficiently symptomatic by clinical measures, the heart may be diagnosed as cardiomyopathic, a form of heart failure. In such a situation, a doctor can recommend mechanical assistance among the few therapeutic options that include pharmacologic therapy and heart transplantation. Where an afflicted person is scheduled to receive a transplant, mechanical assistance may be a choice of therapy until a donor heart becomes available. However, monitoring an implantable device and/or organ of a patient may be difficult and therefore, there may be a need to provide for a monitoring means to monitor an organ and/or implantable device.

Blood pumps are commonly used to provide mechanical augmentation to the pumping performed by the left and/or right ventricles of the heart. Ventricular assistance may be provided by an implantable pump that is connected in parallel with the person's heart and may be regulated by a controller. The controller and the pump use a power source, such as one or more external batteries or electrical connection to a wall socket. A blood pump generally uses about 1-10 W of power. Connection to a sufficient power source to operate the pump and controller can make mobility difficult, which can reduce the quality of life for a patient.

In view of the known problems, it may be advantageous to provide for an improved percutaneous lead.

Any discussion of the prior art throughout the specification should in no way be considered as an admission that such prior art is widely known or forms part of common general knowledge in the field.

SUMMARY

Problems to be Solved

It may be advantageous to provide for an improved percutaneous lead.

It may be advantageous to provide for a percutaneous lead with a plurality of electrodes and/or sensors mounted thereon.

It may be advantageous to provide for an implantable lead which can provide for an electrical communication between an implantable device and a controller.

It may be advantageous to provide for a lead with electrodes and/or sensors near to an organ to monitor the organ and collect data.

It may be advantageous to provide for a lead with at least one sensor to detect acceleration of an organ.

It may be advantageous to provide for a lead with at least one sensor to detect electrical signals of an organ.

It is an object of the present invention to overcome or ameliorate at least one of the disadvantages of the prior art, or to provide a useful alternative.

Means for Solving the Problem

A first aspect of the present invention may relate to a lead assembly for an implantable device. The lead assembly comprising a sheath with a plurality of wires extending from a proximal end and a distal end. The distal end may have at least one electrode fixed thereon. The electrodes may be in communication with sensor electronics; and wherein at least one electrode is on the outer layer of the lead assembly in which the electrode may be used to detect at least one of acceleration and electrical signals of an organ.

Preferably, the lead assembly comprises a first portion and a second portion connected via a connector pair. Preferably, the lead assembly has a relatively thinner region intermediate the proximal end and the distal end. Preferably, the proximal end of the lead may be connected to a controller. Preferably, the plurality of wires may be housed in a lumen. Preferably, the lumen may be a bundle formed from an insulative polymer. Preferably, the sensor electronics may be encapsulated in one of the following locations; the controller, the lead, and the implantable device. Preferably, the electrodes may be fixed to a conductor which extends from a lumen of the lead and through the sheath. Preferably, the sensor electronics may further comprise an analogue-to-digital converter. Preferably, the lead assembly further may comprise a reinforcing element. Preferably, a textured surface is provided on an external surface of the lead for promoting tissue growth.

Another aspect of the present disclosure may relate to a lead assembly for an implantable device. The lead assembly comprising a sheath with a plurality of wires extending from a proximal end and a distal end. The distal end may have at least one electrode fixed thereon. The electrodes may be in communication with sensor electronics; and wherein an aperture is formed in the sheath in which a conductor is in electrical communication with the at least one electrode such that electrical signals of an organ can be detected by the sensor and data can be transmitted to the sensor electronics to be analysed.

Preferably, the sensor electronics may comprise a control module, a sensing module, a memory and a power source. Preferably, the sensor electronics may be encapsulated in the lead. Preferably, the conductor may be within a lumen in the lead assembly. Preferably, the lead assembly comprises a first portion and a second portion, in which the first and second portions may be connected together via a connector pair. Preferably, the memory may store a log of sensed signals. Preferably, the lead further comprises at least one electrical wire extending from the proximal end to the distal end.

In the context of the present invention, the words "comprise", "comprising" and the like are to be construed in their inclusive, as opposed to their exclusive, sense, that is in the sense of "including, but not limited to".

The invention is to be interpreted with reference to the at least one of the technical problems described or affiliated with the background art. The present aims to solve or ameliorate at least one of the technical problems and this may result in one or more advantageous effects as defined by this specification and described in detail with reference to the preferred embodiments of the present invention.

BRIEF DESCRIPTION OF THE FIGURES

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 4 illustrates an embodiment of an electrode arrangement and component arrangement;

FIG. 5 illustrates another embodiment of an electrode arrangement and component arrangement.

DESCRIPTION OF THE INVENTION

Preferred embodiments of the invention will now be described with reference to the accompanying drawings and non-limiting examples.

Figure 1:
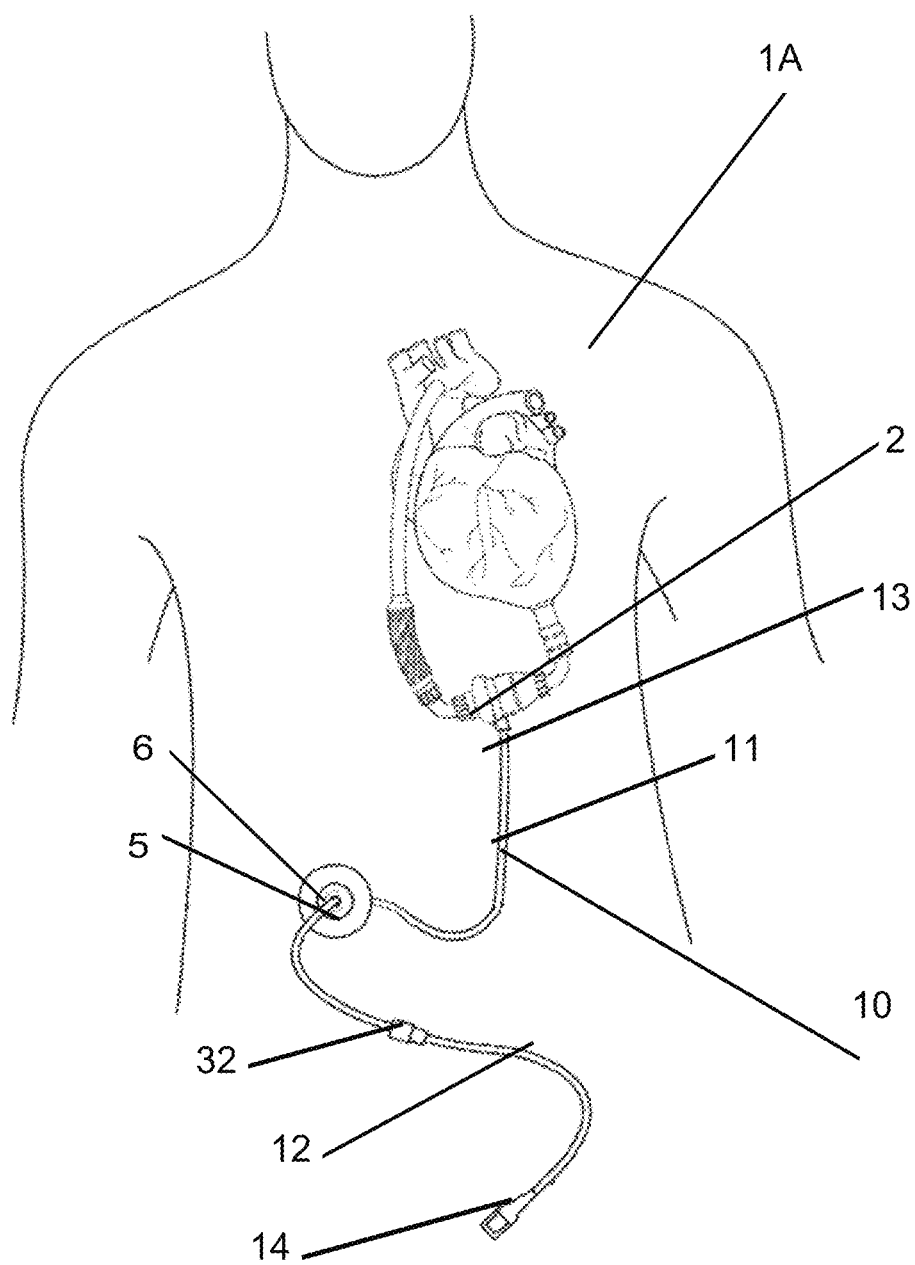
FIG. 1 illustrates an embodiment of an assistance device connected to a percutaneous lead implanted in a patient.

The present invention generally relates to an improvement to percutaneous lead assemblies 10. A first preferred embodiment of this invention is illustrated in FIG. 1. As shown, patient 1 is implanted with a medical assist device 2 to assist or enhance a body function of the patient, for example, the device 2 such can be used to assist with regulation of a heart. Preferably, this medical assist device 2 may be active or passive and may require uni- or bi-directional data, instructions, and/or power in the form of electrical signals from the external environment. Preferably, these electrical signals may be communicated by an external controller 7. It may be preferable to use this embodiment in conjunction with an implantable blood pump or a left ventricle assist device 2. However, it will be appreciated that any implantable device may be used with at least one embodiment of the percutaneous lead assembly 10 of the present disclosure.

As illustrated, lead assembly 10 extends from the device 2 and extends below the floating ribs and out of the patient. In other instances, however, lead assembly 10 may be implanted such that it is offset laterally from the centre of sternum. In some instances, lead assembly 10 may extend laterally enough such that all or a portion of lead assembly 10 is underneath/below the ribcage in addition to or instead of sternum.

The elongated lead body of lead assembly 10 contains one or more elongated electrical wires (see FIGS. 2 and 3) that extend within the lead assembly 10 from the connector at the proximal lead end to electrodes 30 located along the distal portion of lead assembly 10. The elongated lead assembly 10 may have a generally uniform shape along the length of the lead, but may have at least one region which is relatively thinner. The region may be adapted to extend through a port of the skin 6 to minimise a hole 5 diameter. In one example, the elongated lead assembly 10 may have a generally tubular or cylindrical shape along the length of the lead assembly 10. The elongated lead assembly 10 may have a diameter of between 3 and 9 French (Fr) in some instances. However, lead diameters of less than 3 Fr and more than 9 Fr may also be utilized. In another example, the distal portion (or all of) the elongated lead body may have a flat, ribbon or paddle shape. In this instance, the width across the flat portion of the flat, ribbon or paddle shape may be between 1 and 3.5 mm. It will be appreciated that other lead shapes and configurations may be utilised. The lead assembly 10 may be formed from a non-conductive material, including silicone, polyurethane, fluoropolymers, mixtures thereof, and other appropriate materials, and shaped to form one or more lumens within which the one or more conductors extend. Further, chitosan may be used to promote tissue growth, reduce the potential for bacteria to form and reduce infection. The chitosan may be mounted on a textured surface or on the lead at a predetermined location.

Optionally, the lead assembly 10 may also be adapted to energise electrodes 30 for providing therapy to a heart 1A of a patient 1. The electrodes may be all the same type of electrodes 30, or may be any predetermined selection of different electrodes 30. Hence, it is to be understood, that the present invention may be practiced with any form of cardiac stimulation device 2 which includes at least one implantable lead assembly 10, whether that device 2 be a pacemaker, a defibrillation, or a device 2 which combines pacing and defibrillation therapy. Further, the lead assembly 10 may be used to sense electrical signals of the heart via sensors or electrodes 30, and may be used to assist with pulsatility of a pump of the device 2. In addition, the lead assembly 10 may be used to detect the movement of a heart 1A and/or the velocity and/or speed of the heart 1A.

A port 4 of the device 2 is adapted to receive a connector 13 of the lead assembly 10. Preferably, a fluid tight seal is provided at the port 4 and connector 13, such that fluids cannot ingress the device 2. A lock, such as a Luer lock, bayonet fitting or any other suitable medical device lock is provided to securely lock the lead with the device 2 to reduce, or more preferably eliminate, the potential for the lead assembly 10 to inadvertently withdrawn from the port 4. This is of particular concern as the lead assembly 10 will generally have an external portion which may be caught or snagged, and therefore a tension applied to the lead assembly 10 which may be sufficient to remove the lead connector 13 from the port 4. Optionally, a magnetic field may be present to assist with mating of the lead assembly 10 connector with the port of the device 2. In an unillustrated embodiment, the lead may have a sacrificial strain, or a loop strain relief 21, 26 which can extend if tension is applied to the lead assembly 10 and can reduce the potential for the lead assembly 10 to break, be removed unintentionally or damage the skin or organs 1A of a patient 1.

The location at the housing 3 where device connector 13 connects with the port 4 of the housing 3 may prevent coagulation or clotting of blood near to the connection location. Clotting may be prevented by including a texture, or omitting a texture on the surface of the lead assembly 10 and/or the housing 3. Alternatively, the connection location of the device connector 13 with the port 4 may promote tissue growth for accelerated recovery after implantation. A texture on the connector and/or the device 2 proximal the connection location may facilitate tissue growth, and therefore reduce the potential for infections or recovery complications.

The device connector 13 may have a threaded portion which mates with a corresponding threaded region of the port 4 of the device 2. Preferably, the port 4 comprises a female thread and the connector comprises a male thread, such that when mated a fluid tight seal can be provided. Optionally, a protective layer can be disposed on the connector 13 which can assist with forming a fluid tight seal between the port 4 and the connector 13, or a gasket may be provided to be compressed between the device connector 13 and port 4. It is preferred that any protective layer or gasket will be subject to little thermal expansion at temperatures between 15° C. to 45° C. The distal end of the connector 13 is inserted into the port of the device 2 and is inserted until a proximal portion of the thread is within or partially within the port 4. A gasket or seal may also be provided near to the proximal end of the connector 13.

In yet another embodiment, the lead assembly 10 has been formed during the manufacture of the device 2, and therefore removal of the lead assembly 10 is not possible without removing at least a portion of the device 2 housing 3. If the lead assembly 10 is formed with the device 2, the connector 13 is either internal the housing 3 or is omitted, and a seal is provided about a portion of the lead assembly 10 which passes through an aperture formed on the housing 3.

Preferably, the lead assembly 10 comprises a reinforcing element which can reduce the potential for damage to the lead assembly 10 in use. The reinforcing of the lead assembly 10 may be positioned near to a lumen in the lead assembly 10 to reinforce the lumen, and/or may be disposed near to the outer layer of the lead assembly 10. The lumen of the lead assembly 10 may be defined by the bundle 18 and extend from the proximal and to the distal end, or alternatively, the lumen can extend generally parallel to the wire bundle. Optionally, the outer layers of the portions 15, 22 of the lead assembly 10 may be a reinforcing layer, which comprises a weave or braid of reinforcing material. Alternatively, a helical expansion reinforcing may be provided which allows for flexibility of the percutaneous lead assembly 10, and prevents damage from accidental tensile forces and may allow for expansion and contraction in the axial direction. The reinforcement may be a fibre, a metal alloy and/or a composite material. The reinforcing may increase the rigidity of the lead assembly 10, relative to a lead assembly 10 without reinforcing. Other means may also be used to increase the rigidity of the lead assembly 10, such as thickening of the diameter of the lead, or using high tensile materials.

Materials suitable for use with the lead assembly 10 and components thereof may include at least one of the following; polymers, metals and composite materials. Examples of polymers which may be used to form part of the lead may be selected from the following group; PEBAX®, polyether block amide, polyolefin, PTFE, PVC, Silicone, Polyacrylate, Polyester, Polyether, PEEK, Polyamide, Polyurethane, and any other suitable polymers for implantation in a patient.

Examples of metals and/or metal alloys which may be used to form part of the lead may be selected from the following group; stainless steel, cobalt-chromium, titanium, gold, platinum and alloys of any one of the preceding metals. Other biocompatible metals may also be used to form a portion of the lead. Preferably, any metal selected will not poison blood, corrode within the body within a predetermined time period, and will not interfere with electronics internal or external the patient.

Examples of composite materials which may be used to form part of the lead may be selected from the following group; Kevlar, aramid fibre, ceramics, carbon fibre, and any other desired composite material, or fibrous material for use with a ceramic, polymer and/or resin.

It will be appreciated that the above is not an exhaustive list and the materials mentioned are exemplary only. It will be appreciated that any desired materials can be used.

As shown in FIGS. 1 and 4 to 6, the external controller 7 is in electrical communication with the implanted medical device 2 by the use of the flexible percutaneous lead assembly 10. The external controller 7 is or may include any of the following devices: batteries, power supply, hardware controller, personal computer, microcontroller, and/or microprocessors.

The connection formed by the percutaneous lead assembly 10 may allow for the transmission and reception of electrical signals. The lead assembly 10 may allow for a continuous electrical link between the medical device 2 and the controller 7 by the use of continuous wiring running through the core of the lead assembly 10, in which the core may be a lumen or bundle. Preferably, the lead assembly 10 extends from the medical device 2, implanted within the body of the patient 1, through a hole or aperture 5, made by a physician or doctor, to the controller 7.

In another embodiment, the percutaneous lead assembly 10 may also include two connectors. At least one connecter is fixed to the ends of the lead assembly 10 and wherein preferably each connector is designed to mate with a respective corresponding port on the medical device 2 and/or the controller 7. A connector pair 32 is provided to connect the first portion 11 and a second portion 12 of the lead assembly 10 together. The connector pair is formed by connectors 33 and 34.

The percutaneous lead assembly 10 has a first portion 11 and a second portion 4. The second portion 4 may extend from the first connector 3 through the aperture 5 and join with the first portion 11. Preferably, the section of the lead referred to as the second portion 4 may include regions coated with a textured surface. This textured surface may be produced by coating the region of the lead with velour or DACRON™. These types of coating materials promote ingrowth of the patient's cells into the surface of the textured surface and assist in anchoring lead assembly 10 within the patient's body 1. It is also preferred that only lead portions which are to promote growth of tissue are provided with textured surfaces.

Additionally, the second portion 4 extends out from the patient's body 1 through the hole 5. This extension past the hole 5 is shown by relatively thin region. Preferably, region does not include a textured coating. Please note that hole 5 may also be referred to as a permanent exit wound. The hole 5 may also have a skin port 6 installed through which the lead can extend. The skin port 6 may also have a clamping means or retaining means to retain the lead assembly 10 in a desired location. Preferably, the lead assembly 10 passes through the hole 5 and is transcutaneous. It is preferred that the first portion 11 be internal the patient, and the second portion 12 being primarily external the patient. This embodiment depicts the lead assembly 10 including a region which is relatively thinner than the lead portion 12 external of the body of the patient. Wires 20, 27 pass through the centre of the lead assembly 10 and allow electrical communication to be achieved between an external device, such as controller 7, and an internally implanted medical device 2.

Preferably, the relatively thin region is integrally joined to the relatively thick region of first portion 11 and/or the second portion 12. The second portion 12 is also joined to a controller connector 14. When in use, the controller connector 14 may be connected to a controller 7 which is external the patient 1. The controller 7 can be used to monitor data received from the electrodes 30 and monitor at least one of; the device 2, an organ and/or the patient 1 more generally.

The first portion 11 may have the region 11A passing through the exit wound 5 generally allows the exit wound to be of a substantially smaller diameter than otherwise would be the case if the lead assembly was of a uniform thickness. This reduction in the size of the exit wound may lessen the trauma experienced by patient 1 during and after implantation; as well as reducing the chance of infection at or near to the exit wound region. The relatively thick region of first portion 11 of the lead assembly 10 may allow for increased wear resistance of the external portion of the lead as well as providing extra shielding for the wiring within the assembly 10.

Please also note that the first portion 11 may be constructed by wrapping or coating the relatively thin region(s) 11A that extend externally from the patient's body and effectively protect or reinforce the external portion of the lead assembly 10. Additionally, a protective sheath may be used to the first portion 11 to achieve a similar effect of protecting the external portion of the wiring assembly.

Figure 2:
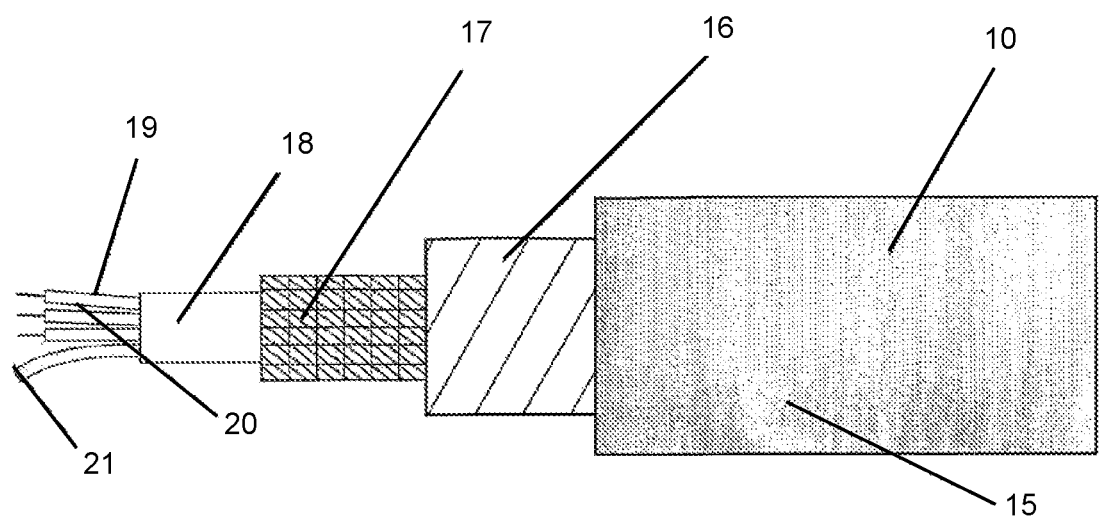
FIG. 2 illustrates an embodiment of a sectional view of a first portion of a percutaneous lead.

A preferred embodiment shown in FIG. 2 depicts a cross sectional cut away view of the first portion 11 of lead assembly 10. In this embodiment, the first portion 11 of the lead assembly 10 may include: an outer protective sheath 15, an inner protective sheath 16, an electromagnetic shielding layer 17, and a wire bundle 20.

Preferably, the outer protective sheath 15 is constructed from a tough but flexible material that is preferably wear resistant and/or cut resistant. The outer protective sheath 15 may be constructed of polyurethane material. Please note that the materials used to construct the first portion 11 of the lead assembly do not need to be biocompatible and may even be toxic during implant conditions. This is because the first portion 11 is preferably not implanted within the body of the patient.

The inner protective sheath 16 provides additional wear resistance. Generally, the inner protective sheath 16 may function to support the general shape and configuration of the first portion 11. Preferably, the inner protective sheath 16 is flexible yet resistant to wear. In some preferred embodiments of the present invention, the inner protective sheath 16 may be constructed of silicone rubber or another predetermined polymer which may be relatively transparent and enable easy inspection as to the condition and quality of the inner protective sheath 16.

The electromagnetic shielding layer 17 may be included within the structure of the first portion 11 of the lead assembly. This layer 17 may function to prevent electromagnetic interference from the outside environment interfering with the electric signals being communicated by the lead assembly, when in use. The electromagnetic shielding layer 17 is preferably constructed from braided stainless steel and this is because metals generally provide the most efficient electromagnetic shielding 17. Additionally, stainless steel braid is relatively wear resistant and cut resistant, which prevents accidental breakage by a patient, user or doctor. Also, stainless steel is generally resistant to oxidation or rusting and is therefore preferred for long term applications in vigorous environments and is also suitable for implantation.

Within the electromagnetic shielding layer 17 may be a wire bundle 20 which contains the wires to act as an electrical conduit for the lead assembly. The wire bundle is generally assembled by inter weaving several insulated wires 18 with each other and a wiring strain relief 21. The position of the wires 20 and the mechanical strain relief 21 can be set in place using second layer of silicone. Preferably, the lead assembly 10 includes three wires 19, but any number of wires 19 may be used. An increase in the number of wires 19 will typically increase the overall minimum diameter of the lead assembly 10; however a reduction of the wire diameters may assist with reduction of the diameter of the lead assembly 10. It may be advantageous to provide for a lead assembly with fewer insulated wires to provide functionality to the implantable medical device, while also having at least one redundant wire in the event that one wire is faulty or becomes damaged. Preferably, the strain relief 21, 26 is constructed from Kevlar™ cords or another material which has desirable tensile yield strength in the range of 50 MPa to 5000 MPa, and more preferably in the range of 150 MPa to 4000 Mpa. Additionally, the wires 16 within the wire bundle 20 should be separately insulated preferably using Perfluoroalyoxy ('PFA') insulation 19.

Figure 3:
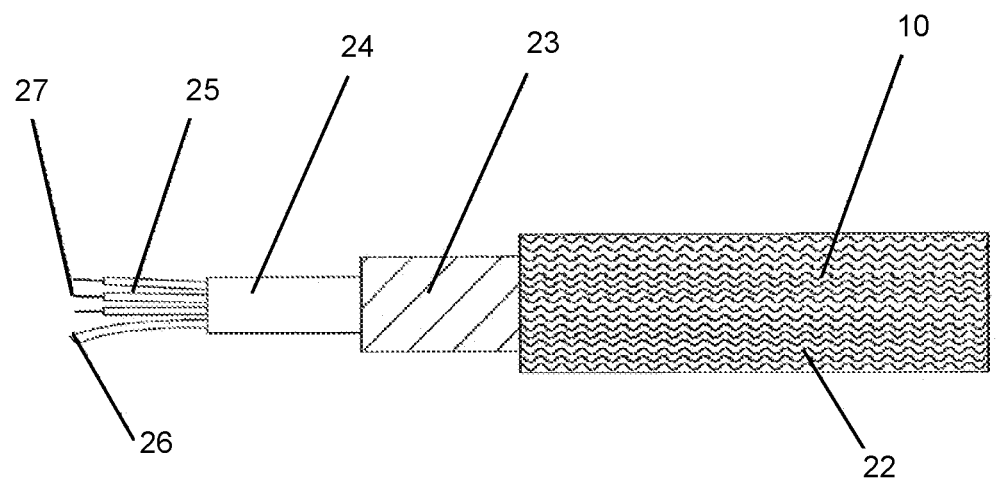
FIG. 3 illustrates an embodiment of a sectional view of a second portion of a percutaneous lead.

A further embodiment is shown in FIG. 3 and depicts the second portion 12 of the lead assembly 10. The second portion 12 may include a textured outer surface 22, outer protective layer 23, and a wire bundle 24.

Preferably, at least a section of second portion 12 is covered with a textured outer surface 22. The textured outer surface 22 may be constructed of velour or Dacron™. This textured surface 22 may permit a patient's body to ingrow into regions of the lead assembly covered with this textured surface 19. It may also be noted that the textured surface preferably may cover predetermined regions of the lead assembly 10. Preferably, the textured region is located at, and/or proximal the location where the lead assembly 10 is to be anchored to the body of the patient 1. Portions of the region 11A which extend externally from the patient 1 may not require a textured surface for this reason.

The outer protective layer 23, in this embodiment, performs a similar function of the inner protective sheath 16 of the first portion 11 described in relation to FIG. 3. The outer protective layer 23 adds further wear resistance, may be flexible, may be substantially biocompatible and may be suitable for implantation. The outer protective layer 23 may be constructed of silicone or another polymer. Beneath the outer protective layer 23 preferably is a wire bundle 22. This wire bundle 22 may include: three wires 27 (which are preferably covered with insulation 25), a wiring strain relief 24, and some silicone to provide dimensional support. The wire bundle 24 may be constructed in similar manner to the wire bundle 17 as shown in FIG. 2.

The smaller or thinner diameter of second portion 12 may also increase the anchoring effect of the textured surface, as the thinner region may allow for better tissue integration. The smaller or thinner diameter may be accomplished by the removal of outer protective layer 23 and a shielding layer, similar to that of shielding layer 17 of the first portion. The shielding layer 17 may not be required for communicating electrical signals with a medical device, particularly in cases where the length of the relatively thin region 11A of the lead assembly 10 is relatively short when compared against the exposed regions of the lead assembly 10 which are external to the patient, such as second portion 12.

Preferably, the lead assembly 10 includes a region 11A coated with a textured surface 4, in which the region 11A is of a relatively smaller diameter than the lead portions either side, such that the diameter of hole 5 can be minimised. Having the lead portions either side of the region 11A of a relatively larger diameter, the region can be retained in the hole 5 and axial movement of the lead assembly 10 can be prevented or minimised. Additionally, the size of the hole 5 is minimised because of the thickness of the region which passes through the hole 5. It will be appreciated that the lead section adjacent to the region is relatively thicker than the region. This minimisation of the thickness of the region reduces the probability of infection and promotes wound healing after implantation as the hole 5 formed in the skin is relatively smaller than if the lead were of a uniform size.

In yet another embodiment, the lead assembly 10 includes a strain terminator mechanism. The skin of a patient at a site 5 where the lead assembly 10 exits the body. The lead assembly, in this embodiment includes of a relatively thin region and a second portion 11, joined by two connectors 33 and 34. Preferably these connectors mate to form a connection and allow electrical communication of the wires 20, 27 within the lead assembly 10.

Preferably, connectors 33 and 34 are submersible and/or water resistance. This water resistance feature will allow the patient to bath, shower or swim in relative safety in regard to medical device failure or electrocution. This may be achieved by including two 'O' rings within the connectors so as to provide a relatively good seal against water penetration. The connectors preferably are made of wear resistance plastic material which is lightweight and unlikely to cause discomfort to the patient. It may also be preferable to allow the connectors to be secured together, when in use, by a screw & thread means.

It may also be preferable for the connectors 33 and 34 to allow for easy replacement of the second portion 11, in situations of accidental breakage without requiring the patient to undergo substantive invasive surgery. This may be achieved by disconnecting the connectors 33 and 34 and then attaching a replacement second portion 11 of the lead assembly.

The strain relief mechanism is arranged so that if the lead assembly is accidentally or otherwise pulled, the lead assembly is not pulled from the patient's body. Additionally, the implanted medical device, which the lead assembly is connected internally to, may also be damaged by such an accident or incident. In situations where the lead is pulled, the connectors 33, 34 may separate from the force before damage can be imparted to the lead and/or the skin of the patient. This may overall reduce the potential for serious injuries to occur from accidental tensions on the lead assembly 10.

The percutaneous lead assembly 10 can include a distal end 28 located internal to the user and a proximal end 29 located external to the user, with a portion that traverses the skin of a patient. The proximal end 29 can be electrically connected to the controller 7 and the proximal end 29 can be removably coupled to an external power supply (not shown). A connector (not shown) can be used to protect the external physical structure of the proximal end 28, as well as the exposed metal connections that can be coupled to the external power supply. In some embodiments, this connector can be designed to be fluid resistant (or fluid proof). In some embodiments, the connector can prevent moisture from seeping into the lead and reaching the metal connections. The connector can also to prevent any electrical conduction from any outside element with the metal connections. In some embodiments, the connector can be waterproof and fluid resistant. The connector structure can be made of a metallic or non-conducting material; in either case, the connector design will have insulation to prevent shorting of the metal connections or conduction of electricity between an external source and the metal connections. When connected to an external power supply, power sufficient for the normal operation of the device 2 can be transferred through the percutaneous lead assembly 10 by the wires of the lead. When the percutaneous lead assembly 10 is disconnected from an external power supply, power for the normal operation of the device 2 can be supplied by an internal rechargeable power storage device.

The proximal end 29 of the percutaneous lead assembly 10 can be electrically coupled to an external power source. In these circumstances, the external power source can supply power for normal operation of the internal components of the device 2 (e.g., the pump, the controller 7, and the like) and to recharge power storage device of the device 2 or the sensor electronics 35. The external power source can be in the form of external batteries, an external power source plugged into a traditional wall socket such that it can convert AC electricity to DC electricity, and the like. For example, when the percutaneous lead assembly 10 can be coupled to an external power source that is plugged into a wall socket, the user is limited in the distance that he can travel. In these circumstances, the user may be limited to a single room, a single building, and the like. Furthermore, due to the connection of the percutaneous lead assembly 10 to the external power source, the user may be limited from performing activities requiring a high degree of freedom of physical movement and/or that involve exposure to liquids, including but not limited to daily activities such as taking a bath, grocery shopping, physical and sporting activities like swimming, golf, tennis, etc., and household maintenance.

In yet another embodiment, the lead assembly 10 is connected to a portable external power source, such as external batteries and/or the controller 7. Using external batteries in combination with an internal battery may provide for an improved quality of life for a patient.

The device 2 may be used to provide assistance to a cardiovascular system or more generally to a heart of a patient. While it will be appreciated that other devices 10 may be suitable for use with the lead assembly 10, specific reference will be made with respect to ventricle assist devices, pacing devices and other heart assistance devices.

Device 2 may include a housing 3 that forms a hermetic seal that protects components of device 2. The housing 3 may be formed of a biocompatible material, such as titanium. Optionally, the housing 3 may be used as an electrode for detection of electrical signals or another desired electrode function. Device 2 may also include a connector assembly (also referred to as a connector block or header) that includes electrical feedthroughs through which electrical connections are made between lead assembly 10 and electronic components included within the housing 3. An electrical component module may be used to house one or more processors, memories, transmitters, receivers, sensors, sensing circuitry, therapy circuitry, power sources and other appropriate components. The electrical component module may be located within the housing 3, within the lead assembly 10, or external the patient in a controller for the electronics.

The housing 3 is configured to be implanted subcutaneously in a patient, and lead assembly 10 can be implanted percutaneously with a distal end being in communication with the device 2, and the proximal end being external the patient body and preferably connected to a controller and/or power source. Device 2 may, in some instances, be implanted in the left ventricle of the patient.

Lead assembly 10 includes an elongated lead body having a proximal end that includes a connector (not shown) configured to be connected to device 2 and a distal portion that includes electrodes 30. The electrodes 30 on the distal portion of the lead assembly 10 are preferably subcutaneous and are positioned near to the device 2. The electrodes 30 may be spaced from the device 2 and the organ (in one example, a heart), and may not be in physical contact with the organ and/or the housing 3 of the device 2.

The distal portion of lead assembly 10 is described herein as being connected with device 2. Thus, points along the distal portion of lead assembly 10 may extend near to the heart or other organ which receives the device 2. It will be appreciated that the most distal portion 28 of the lead assembly 10 may be installed proximal the pericardium. In other embodiments, the distal portion of lead assembly 10 may be implanted in other non-vascular, extra-pericardial locations, including the gap, tissue, or other anatomical features around the perimeter of and adjacent to, but not attached to, the pericardium or other portion of heart. In other words, the distal portion of lead assembly 10 may be implanted in the region around the outer surface of heart, but not attached to heart 1A.

Optionally, the lead assembly 10 comprises a radiopaque marker which can assist with determination of the location of the lead assembly 10 and/or the electrodes thereon. The radiopaque marker may be on the surface of the lead assembly 10, or may be deposited below the outer layer of the lead assembly 10. The diameter of the lead assembly 10 may be in the range of 3 Fr to 34 Fr, but more preferably is in the range of around 7 Fr to 17 Fr.

The lead assembly 10 may comprise at least one redundant electrode 30, wire 20, 27 or conductor 31, which may be activated in the event that the redundant electrode or conductor fails. The electrodes 30 may be disposed on the outer sheath 15 in any predetermined array or spacing. Spacing of the electrodes 30 can be at any predetermined interval, or may be at any predetermined spacing. For example, electrodes may be dot electrodes and may be arranged in a lattice formation, or the electrodes may be ring electrodes or strip electrodes spaced at predetermined longitudinal intervals. The longitudinal direction of the lead assembly 10 is the axial direction of the lead.

The electrodes 30 may be attached to the sheath 15 by swaging or crimping. Other methods may be used to fix the electrodes to the sheath 15. An aperture can be formed through the sheath 15 and through to at least one conductive wire within the lead assembly 10.

Attaching the electrodes 30 to the percutaneous lead assembly 10 may require an aperture to be formed such that conductors 31 or wires 20, of the lead assembly 10 can extend through the sheath 15 or textured surface 22. The conductors 31 may also be in the bundle and extend from the bundle to the external surface of the lead assembly 10. The aperture (not shown) may be formed at any location on the lead assembly 10 and more preferably, is formed where an electrode 30 is to be mounted thereon.

The distal portion of lead assembly 10 may be implanted substantially within anterior mediastinum such that electrodes 30 are located near an organ, such as the heart 1A. For instance, the distal end of the lead assembly 10 may be implanted within anterior mediastinum. In one example, the housing 3 can be used to amplify the electrical signals of the heart 1A or can be used to transmit the electrical signals of the heart for the sensors 30 to sense.

An aperture is formed by cutting or boring into the tubular member an outer surface of the tubular member through to the conductor lumen. Distal ends of the conductors 31 are pulled through the aperture to be externally accessible.

An electrically conductive element in the form of a ring electrode 30 may be attached to a distal end of a respective conductor 31. In one embodiment, the distal end of the conductor 31 is secured to its associated ring electrode 30 by inductively welding an end of the conductor 31 to an internal surface of the ring electrode. Induction welding may be desirable as it provides a consistent result, no new materials are introduced by the welding of the conductor to the ring electrode and it eliminates the need for any intermediate materials.

The ring electrodes are chosen to have an inner diameter that approximates the outer diameter of the tubular member so each electrode 30 is a snug fit about an external surface of the lead assembly 10. Once the conductors 31 have been attached to their associated electrodes 30, the ring electrodes 30 can be mounted via the end of the distal end 28 of the lead assembly 10 and positioned at longitudinally spaced intervals. It will be appreciated that any excess length of conductor can be drawn into the lumen of the lead assembly 10 by pulling on the proximal end of the conductor 31.

Once the electrodes 30 have been positioned on the lead assembly 10, the lumen may be charged with a filler material, which serves to insulate the conductors with respect to each other and to inhibit collapse of the conductor lumen during subsequent steps. The filler material is, for example, a flexible ultraviolet (UV) adhesive. Alternatively, the conductors for the electrodes 30 are pre-insulated such that the filler material is not required. The electrodes 30 may be secured in position on the tubular member by means of a suitable biocompatible adhesive, for example, an epoxy adhesive if they are not secured by induction welding.

The one or more elongated electrical conductors 31 contained within the lead body of lead assembly 10 may engage with respective ones of electrodes 30. In one example, each of electrodes 30 is electrically coupled to a respective conductor 31 within the lead body. The respective conductors 31 may electrically couple to circuitry, such as a therapy module or a sensing module, of device 2 via connections in connector assembly, including associated feedthroughs. The sensing module may have a comparison database of regular and/or irregular electrical signals to which sensed signals can be compared to detect irregular signals. Signals detected may be converted from analogue to digital signals via analogue-to-digital converters (ADCs) using predetermined algorithms.

In addition, it should be noted that system 10 may not be limited to treatment of a human patient. In alternative examples, system 10 may be implemented in non-human patients, e.g., primates, canines, equines, pigs, ovines, bovines, and felines. These other animals may undergo clinical or research therapies that may benefit from the subject matter of this disclosure.

The lead assembly 10 has a connector 13 which is adapted to mate with the port 4 for electrically coupling the assist device 2 to the lead assembly 10.

Figure 6:
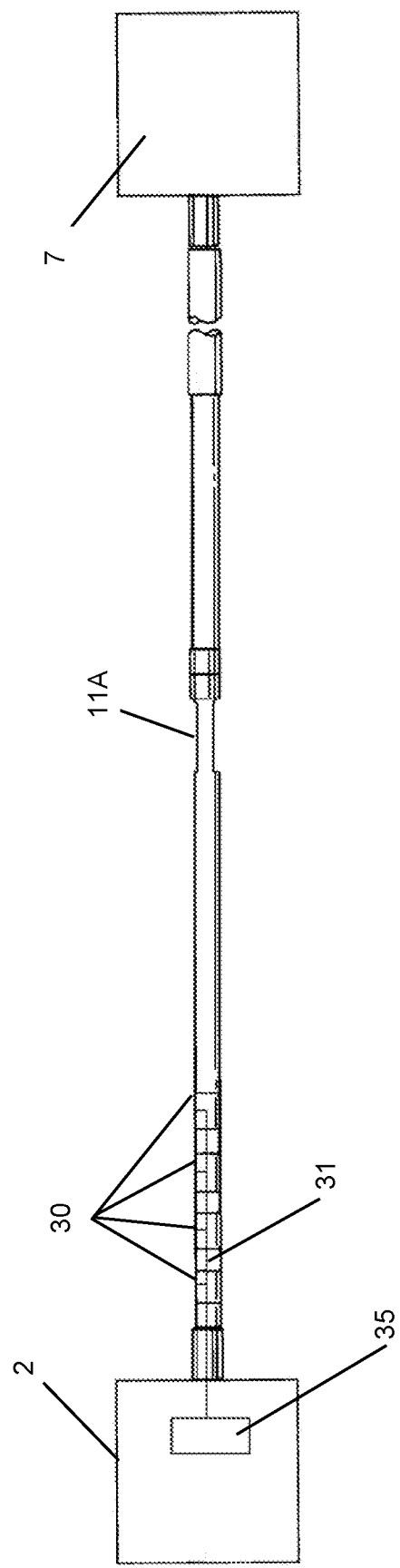
FIG. 6 illustrates a further embodiment of an electrode arrangement and component arrangement.

The lead assembly 10 as illustrated in FIGS. 4 to 6 includes an elongated lead body having a distal end 28 and a proximal end 29. It will be appreciated by those skilled in the art that the lead assembly 10 may include a plurality of electrodes 30. Still further, those electrodes may be pacing electrodes, sensing electrodes, defibrillation electrodes, or a combination of pacing, sensing and defibrillation electrodes. Embodiments of the present invention may be employed to advantage in all such forms of leads.

FIG. 3 shows the strain relief member 26 covered by an insulator coating 48. The insulator 25 may be polyurethane, silicone rubber, ETFE (ethylenetetrafluoroethylene) or PTFE (polytetrafluoroethylene), for example, and serves to protect the strain relief member 26 and to preclude it from electrically contacting any lead components other than those to which it is secured.

Referring to FIG. 4, there is shown an embodiment of lead assembly 10 with sensors mounted on the outer sheath 15. The sensors may be fixed onto the lead assembly 10 by conventional methods, or may be embedded therein by heat treatment methods or by using heat shrink material. Preferably, the sensors are ECG electrodes 30, but may be any other desired sensor 30 to detect electrical signals or detect movement. The sensors are preferably exposed to the anatomy and internal environment of the patient 1. As shown the conductors 31 for the electrodes/sensors 30 extend from the electrodes/sensors 30 back to the controller 7, and are connected to sensor electronics 35, such as ECG electronics and/or accelerometer electronics, similar to the controller electronics described before. Other sensor electronics 35 may be installed which allow for interpretation and recording of detected signals and/or movements.

In another embodiment shown in FIG. 5, there is shown a lead assembly 10 with similar components as that of FIG. 4. However, this embodiment differs in that the sensor electronics 35 are installed in the lead assembly 10. Preferably, the sensor electronics are encapsulated by the lead assembly 10. In this way the sensor electronics 35 can communicate data to the controller via wires or conductors 31, or may be adapted to wirelessly transmit data. Wireless transmission of data may be advantageous if the controller is removed as sensing may still be achieved. This is of particular advantage when external lead portions are being replaced or the controller is being replaced or is otherwise not present. Data transmitted wirelessly may be sent to a personal device, such as a smart phone, personal computer, computer, tablet or other desired device. If the sensor electronics 35 are installed in the lead assembly 10, the portion of the lead with the electronics may be of a relatively larger cross-sectional area than the adjacent portions of the lead. As such, this portion may be covered with a textured outer surface to improve the potential for tissue growth thereon to reduce the movement of the lead assembly 10 internal the patient. The wires of the lead may also pass through the electronics, or be connected with the sensor electronics 35 in the lead assembly 10. Optionally, at least one dedicated conductor 31 is disposed in the lead assembly 10 for communicating data between the sensor electronics 35 and the controller 7.

The thickness of the lead may be relatively larger at the location of the sensor electronics 35, to allow for all electronic components to be installed in the lead 10. Flexible electronic components may also be used to allow for flexure or bending of the lead at the location of the sensor electronics 35.

It will be appreciated that sensors 30 mounted on the lead assembly 10 may have a different polarity such that one sensor may act as a negative terminal and another sensor may act as a positive terminal. In this way electrical signals may be more accurately measured and potential differences may be more accurately detected.

Referring to yet another embodiment as shown in FIG. 6, the sensor electronics 35 are mounted in the device 2. Again, the sensor electronics 35 may be similar to that as previously described herein. If the sensor electronics 35 are mounted in the device 2, the sensor electronics 35 may be adapted for use with the lead sensors and sensors of the device 2. Wires in the lead assembly 10 may be used to transfer data to the controller or other device, or a wireless communication means may be adapted to communicate data. A sensor housing 36 may be provided in the housing of the device or mounted to the exterior of the device housing 3.

The sensor electronics (not shown) may include a control module, sensing module, communication module, memory and optionally a therapy module. The electronics may receive power from a power source, which may be a rechargeable or non-rechargeable battery. The described modules may be implemented together on a common hardware component or separately as discrete but interoperable hardware or software components. Depiction of different features as modules is intended to highlight different functional aspects and does not necessarily imply that such modules must be realized by separate hardware or software components. Rather, functionality associated with one or more modules may be performed by separate hardware or software components, or integrated within common or separate hardware or software components.

Sensing module is electrically coupled to some or all of electrodes 30 via the conductors of lead assembly 10. Sensing module is configured to obtain signals sensed via one or more combinations of electrodes 30 and optionally the housing electrode of device 2 and process the obtained signals.

The components of sensing module may be analogue components, digital components or a combination thereof. Sensing module may, for example, include one or more sense amplifiers, filters, rectifiers, threshold detectors, analogue-to-digital converters (ADCs) or the like. Sensing module may convert the sensed signals to digital form and provide the digital signals to control module for processing or analysis by the controller 7. For example, sensing module may amplify signals from the sensing electrodes and convert the amplified signals to multi-bit digital signals by an ADC. Sensing module may also compare processed signals to a threshold to detect the existence of irregularities within an organ, such as irregular movements or faulty pumping in the case of a heart 1A.

Control module may process the signals from sensing module to monitor electrical activity of heart 1A of patient. Control module may store signals obtained by sensing module as well as any generated EGM waveforms, marker channel data or other data derived based on the sensed signals in memory. The memory may be adapted to log or store sensed data or other predetermined data sets. Control module may analyse the EGM waveforms and/or marker channel data to detect cardiac events which may be adverse to the life of the patient 1. In one embodiment, in response to detecting the cardiac event, control module may control therapy module to deliver the desired therapy to treat the cardiac event, e.g., defibrillation shock, cardioversion shock, ATP, post shock pacing, bradycardia pacing.

Lead assembly 10 may further include one or more anchoring mechanisms that are positioned on the distal end, along the length of the lead body, or near the incision/entry site. The anchoring mechanisms may affix lead assembly 10 to reduce movement of lead assembly 10 from its desired substernal location. For example, the lead assembly 10 may be anchored at one or more locations situated between the distal end and a point along the length of the portion of the lead body extending superior from the xiphoid process under sternum. The one or more anchoring mechanism(s) may either engage fascia, muscle or tissue of patient or may simply be wedged therein to affix the lead to prevent excessive motion or dislodgment. The anchoring mechanisms may be integrated into the lead body. In alternative embodiments, the anchoring mechanisms may be discrete elements formed in line with the lead body, such as a helix, rigid tines, prongs, barbs, clips, screws, and/or other projecting elements or flanges, disks, pliant tines, flaps, porous structures such as a mesh-like element that facilitate tissue growth for engagement, bio-adhesive surfaces, and/or any other non-piercing elements. In addition or alternatively, the lead may be anchored through a suture (e.g., using an anchoring sleeve) that fixedly-secures the lead to the patient's musculature, tissue or bone at the xiphoid entry site. In some embodiments, the suture may be sewn through pre-formed suture holes to the patient.

In yet another embodiment, FIG. 2 may illustrate a section of the second portion 12, and FIG. 3 may illustrate a section of the first portion 11. In this way, the external thickness of the lead assembly 10 is relatively thicker than the internal portion of the lead assembly 10. Alternatively, the thickness of the lead assembly 10 may be generally uniform from the proximal end to the distal end. Optionally, at least one region may be relatively thinner than the thickest portion of the lead, and the region can pass through the hole 5 and skin port 6 installed in the hole 5 of the patient 1.

Although the invention has been described with reference to specific examples, it will be appreciated by those skilled in the art that the invention may be embodied in many other forms, in keeping with the broad principles and the spirit of the invention described herein.

The present invention and the described preferred embodiments specifically include at least one feature that is industrial applicable.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A percutaneous lead assembly for an active implantable device, the lead assembly comprising;
 a sheath with a plurality of wires extending from a proximal end to a distal end, wherein the plurality of wires are housed in a lumen of the lead assembly;
 the sheath having an outer layer, wherein the outer layer has a weave of reinforcing material;
 the wires being adapted to power the active implantable device;
 the distal end having at least one electrode fixed thereon;
 the electrodes being in communication with sensor electronics; and
 wherein the at least one electrode is on the outer layer of the sheath of the lead assembly in which the at least one electrode is used to detect at least one of acceleration and electrical signals of an organ.

2. The percutaneous lead assembly of claim 1, wherein the lead assembly comprises a first portion and a second portion connected via a connector pair.

3. The percutaneous lead assembly of claim 1, wherein the lead assembly has a relatively thinner region intermediate the proximal end and the distal end.

4. The percutaneous lead assembly of claim 1, wherein the proximal end of the lead is connected to a controller.

5. The percutaneous lead assembly of claim 1, wherein the lumen is a bundle formed from an insulative polymer.

6. The percutaneous lead assembly of claim 1, wherein the sensor electronics are encapsulated in one of the following locations: the controller, the lead, and the implantable device.

7. The percutaneous lead assembly of claim 1, wherein the electrodes are fixed to a conductor which extends from a lumen of the lead and through the sheath.

8. The percutaneous lead assembly of claim 1, wherein the sensor electronics further comprise an analogue-to-digital converter.

9. The percutaneous lead assembly of claim 1, wherein a textured surface is provided on an external surface of the lead for promoting tissue growth.

10. A percutaneous lead assembly for an implantable device, the lead assembly comprising;
 a sheath with a plurality of wires extending from a proximal end and a distal end;
 the sheath having an outer layer, wherein the outer layer has a weave of reinforcing material;
 the distal end having at least one electrode fixed thereon; wherein at least one electrode is on the outer layer of the sheath of the lead assembly; and
 the at least one electrode is used to detect at least one of acceleration and electrical signals of an organ;
 the at least one electrode being in communication with sensor electronics; and
 wherein an aperture is formed in the outer layer of the sheath in which a conductor is in electrical communication with the at least one electrode such that electrical signals of an organ can be detected by the sensor and data can be transmitted to the sensor electronics to be analysed.

11. The percutaneous lead assembly of claim 10, wherein the sensor electronics comprise a control module, a sensing module, a memory and a power source.

12. The percutaneous lead assembly of claim 11, wherein the memory can store a log of sensed signals.

13. The percutaneous lead assembly of claim 10, wherein the sensor electronics are encapsulated in the lead.

14. The percutaneous lead assembly of claim 10, wherein the conductor is within a lumen in the lead assembly.

15. The percutaneous lead assembly of claim 10, wherein the lead assembly comprises a first portion and a second portion, in which the first and second portions are connected together via a connector pair.

16. The percutaneous lead assembly of claim 10, wherein the lead further comprises at least one electrical wire extending from the proximal end to the distal end.

* * * * *